United States Patent [19]
White et al.

[11] Patent Number: 5,810,593
[45] Date of Patent: Sep. 22, 1998

[54] THREE-DIMENSIONAL ORNAMENTAL DENTAL APPLIANCE JEWELRY AND METHOD FOR ATTACHING IT DIRECTLY TO THE SURFACE OF A TOOTH

[76] Inventors: Stephan A. White, 5220 N. Main St., Kansas City, Mo. 66118; Patricia A. Wobker, 38669 W. 319th St., Paola, Kans. 66071; Mary L. Kahler, 5620 Woodson, Raytown, Mo. 64133

[21] Appl. No.: 650,180

[22] Filed: May 20, 1996

[51] Int. Cl.⁶ ........................................ A61C 13/08
[52] U.S. Cl. ........................................ 433/206; 433/219
[58] Field of Search ........................ 433/206, 207, 433/215, 218, 219, 223, 229, 8, 9, 10, 11, 12, 13, 14, 15, 16, 17; 63/2, DIG. 1

[56] References Cited

U.S. PATENT DOCUMENTS

| | | | |
|---|---|---|---|
| 1,711,402 | 4/1929 | Berger | 433/223 |
| 1,803,680 | 5/1931 | Schwartz | 433/223 |
| 3,521,355 | 7/1970 | Pearlman | 433/3 |
| 3,916,526 | 11/1975 | Schudy | 433/8 |
| 4,523,908 | 6/1985 | Drisaldi et al. | 433/3 X |
| 4,735,569 | 4/1988 | Munk | 433/213 |
| 4,741,700 | 5/1988 | Barabe | 433/229 |
| 5,011,410 | 4/1991 | Culler et al. | 433/208 |
| 5,104,320 | 4/1992 | Stoll | 433/206 |
| 5,542,842 | 8/1996 | Andreiko et al. | 433/3 |

OTHER PUBLICATIONS

"Teeth inlaid with Jade, Tourquoise, Pyrite, Etc.,"The Washington Post Mar. 18, 1973, pp. E10–E11.

*Primary Examiner*—Nicholas D. Lucchesi
*Attorney, Agent, or Firm*—Kenneth W. Iles

[57] ABSTRACT

A process for producing and installing a three-dimensional ornamental jewelry dental appliance onto a target tooth selected by the patient without employing a crown is disclosed, as is the structure of the ornamental appliance itself. The dental appliance is made by making an impression of the target tooth, creating a mold from that impression and casting a noble metal appliance from a lost wax mold having a rear wall that conforms exactly to the surface of the target tooth. Registration of the ornamental appliance with a target area of the target tooth is assured by use of an indexing tab integrally molded with the ornamental appliance. The rear surface of the dental appliance and surface of the tooth are etched to improve bonding. A dentist applies a cement to the rear surface of the ornamental appliance and a catalyst to the tooth, then presses the dental appliance against the tooth and removes the indexing tab.

3 Claims, 3 Drawing Sheets

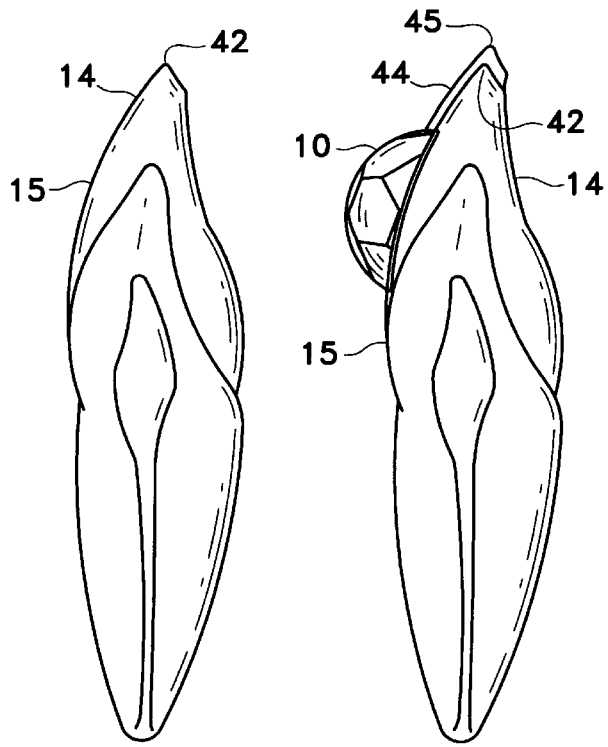
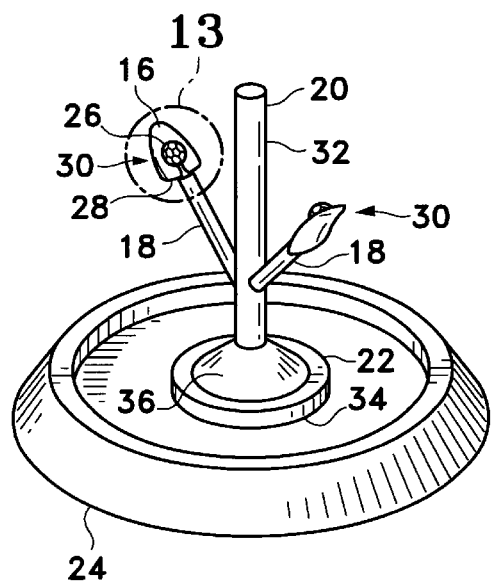
FIG. 6  FIG. 7  FIG. 8
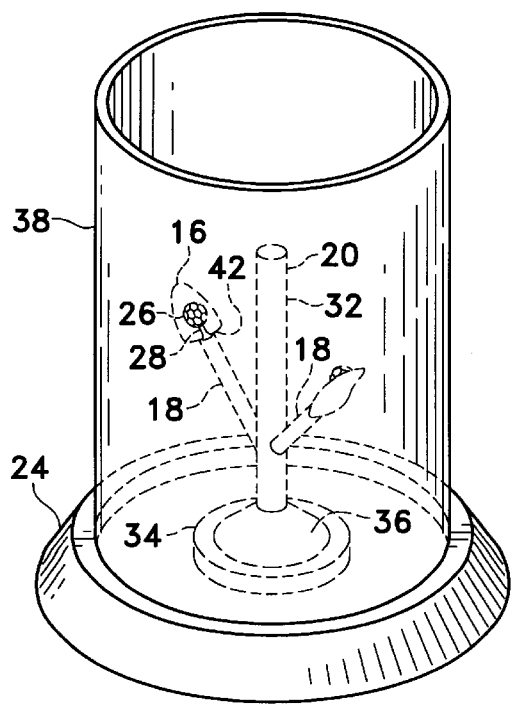
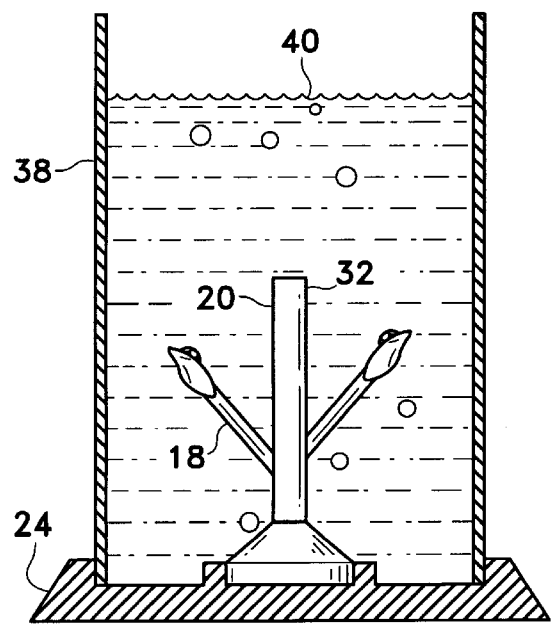
FIG. 9  FIG. 10

THREE-DIMENSIONAL ORNAMENTAL DENTAL APPLIANCE JEWELRY AND METHOD FOR ATTACHING IT DIRECTLY TO THE SURFACE OF A TOOTH

BACKGROUND OF THE INVENTION

1. Field of the Invention

The present invention is related to a process for making and attaching ornamental jewelry directly to the surface of a living tooth, crown, bridge, or the like. More particularly, the present invention is related to a process for attaching a three-dimensional jewelry piece to the surface of a living tooth without the need for extensive surface preparation and matching the back surface of the appliance with the tooth's surface for more secure adhesion.

2. Description of Related Art Including Information Disclosed Under 37 C.F.R. Sections 1.97–1.99.

In certain social circles, it is popular to wear teeth crowns with ornamental designs attached to them. Typical designs might include, for example, dragons, initials of the person or someone close to him, symbols of the zodiac, animals, and so forth. Typically such crowns are made from yellow gold and are attached over upper or lower front teeth, where they are clearly visible to anyone looking at the wearer.

To install such ornamental crowns, as is the case with all crowns, the tooth on which the ornamental crown is to be mounted must be mutilated and reduced to a small stump. Most dentists are reluctant to install such ornamental crowns because the tooth that is selected for this treatment is normally a healthy tooth and dentists usually do not want to mutilate healthy teeth. Dentists regard this as an extreme procedure for ornamental purposes. Further, crowns are difficult to replace, should the user desire to change the design or the like.

An alternative type of ornament for teeth is described in U.S. Pat. No. 5,104,320, issued to Stoll on Apr. 14, 1992, which describes a process for attaching a design made from thin foil to a tooth. This process relies on the use of force from the dentist's hand to conform the design to the tooth, requiring the use of thin malleable foil and thereby severely limiting the nature and prominence of the design that can be installed on a tooth.

Therefore there is a need for a process that allows a three-dimensional ornamental jewelry dental appliance to be attached directly to the surface of a tooth, crown, bridge or the like without any standard tooth preparation commonly used for other procedures, such as in the application of tooth veneers; that provides a custom fit for the target tooth, thereby providing a better and permanent bond in ordinary use; and that can be removed, leaving the tooth nearly normal in appearance and function, when removed properly and that can be replaced with a different design.

SUMMARY OF THE INVENTION

Accordingly, it is a primary object of the present invention to provide a three-dimensional ornamental jewelry dental appliance that can be attached directly to the surface of a tooth, crown, bridge or the like.

It is another object of the present invention to provide such an appliance that can be installed without traditional preparation of the tooth as used in attaching veneers and the like.

It is another object of the present invention to provide such a dental appliance that provides a custom fit to the target tooth and thereby enable a permanent bond in ordinary use.

It is an other object of the present invention to provide such a dental appliance that can be removed leaving the tooth in a normal appearance, or that can be replaced with another design.

In brief, the process includes taking an impression of the tooth the patient selects for ornamentation, and then pouring a positive of that tooth in refractory material. The desired design or ornamental dental appliance is then waxed onto the positive refractory of the tooth in the position in which the finished design will be applied. The wax design and refectory tooth to which it has been applied are then invested for a lost wax technique of jewelry making and the design is cast in high noble yellow gold or other etchable metals approved for human oral use by the American Dental Association. The rear surface of the appliance conforms exactly to the texture and contour of the target tooth. The mold runner from the sprue lead to the appliance is retained when the appliance is removed from the mold, and serves as an indexing member that is placed over the incisal edge of the target tooth, insuring accurate registration of the appliance with the target tooth, providing a certain and permanent fit with minimal adhesive between the target tooth and the appliance.

The design is cleaned and the rear surface, that is, the surface that will be attached to the tooth, is acid etched. The surface of the tooth is then etched and the design is attached to it by a permanent adhesive.

The ornamental appliance can be removed by prying the appliance off to reveal a tooth normal in appearance and function. Alternatively, the ornamental design can be removed and replaced with another design. An ornamental appliance according to the present invention may be applied to healthy teeth, porcelain crowns, denture teeth or gold crowns, including those previously installed in the patient's mouth.

This method is different from applying tooth veneers, Maryland bridges and the like in that no surface preparation of the tooth is necessary, i.e., there is no cutting down of the tooth surface and the rear surface of the appliance matches the contour and texture of the tooth and is applied in exact registration with the molded area.

It is believed that this method will provide dentists a more palatable alternative to the use of crowns on healthy teeth for people who want a jewelry dental appliance attached to a tooth.

Other objects and advantages of the present invention will become apparent from the following description taken in connection with the accompanying drawings, wherein is set forth by way of illustration and example, the preferred embodiment of the present invention and the best mode currently known to the inventors for carrying out their invention.

BRIEF DESCRIPTION OF THE DRAWINGS

FIG. 6 is a right-hand side elevation of a the left-hand tooth of FIG. 3 shown without an attached ornamental appliance.

FIG. 7 is the tooth of FIG. 6 with an attached ornamental appliance.

FIG. 8 is a right-hand front perspective view of a model tooth set in a sprue base.

FIG. 9 is a right-hand front perspective view of a model tooth set in a sprue base shown with the flask in position.

FIG. 10 is a side elevation of the sprue and flask of FIG. 9 shown after investing.

DETAILED DESCRIPTION OF THE PREFERRED EMBODIMENTS

As required by the Patent Statutes and the case law, the preferred embodiment of the present invention and the best mode currently known to the inventors for carrying out their invention are disclosed in detail herein. The embodiments disclosed herein, however, are merely illustrative of the invention, which may be embodied in various forms. Therefore, specific structural and functional details disclosed herein are not to be interpreted as limiting, but merely to provide the proper basis for the claims and as a representative basis for teaching one skilled in the art to which the invention pertains to make and use the apparatus and process disclosed herein as embodied in any appropriately specific and detailed structure.

Figure 1:
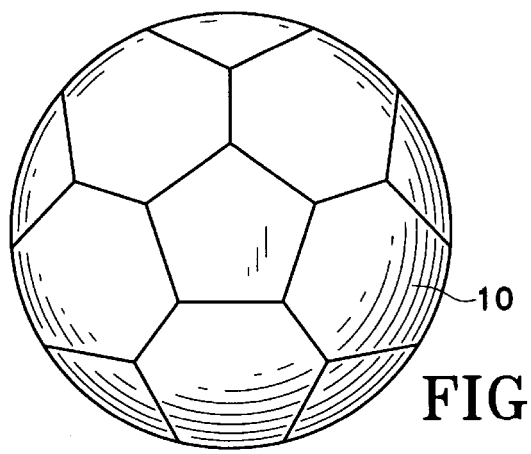
FIG. 1 is a front perspective view of a typical three-dimensional ornamental jewelry design appliance for use with the present inventive process.
Figure 2:
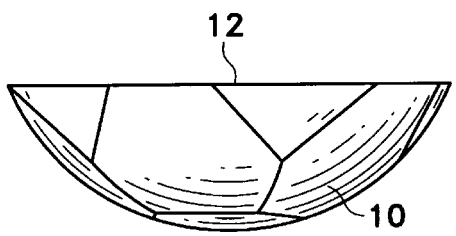
FIG. 2 is a top plan view of the ornamental jewelry design appliance of FIG. 1.

Referring to FIGS. 1 and 2, there is shown an ornamental jewelry dental appliance 10 on the in the shape of a soccer ball, which is cast from gold and has a depth of 1–4 mm. The appliance 10 can be any ornamental shape desired, for example, the baseball appliance 11 shown in FIG. 3, a letter, number, dragon, seahorse, lion's head, sphinx, or the like. The shape of the desired appliance is selected by the patient during a dental visit from a catalog of standard designs. Alternatively, a custom appliance can be designed at the request of the patient.

Figure 3:
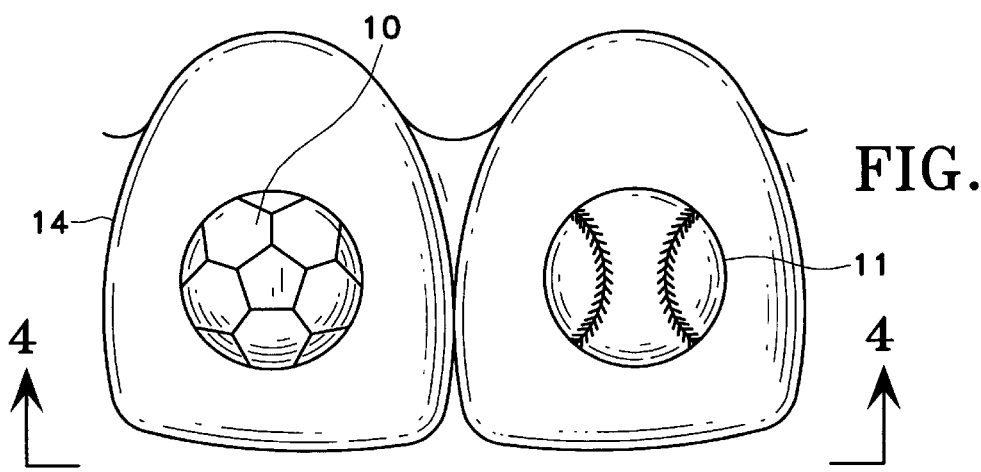
FIG. 3 is a front elevation of the front teeth of the upper jaw of a person showing two ornamental dental appliances installed according to the present invention.
Figure 4:
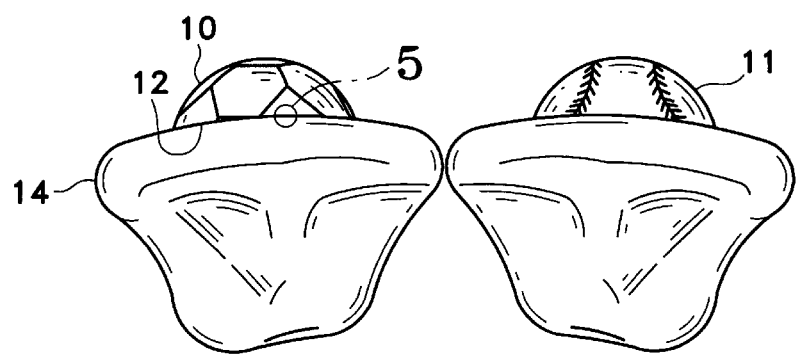
FIG. 4 is a cross sectional view taken along the line 4—4 of FIG. 3.

Referring to FIG. 3, The dentist takes an impression of the target tooth 14 that the patient selects for ornamentation. The tooth impression is a negative or cavity mold. The resulting negative dental impression is sent to a dental laboratory along with a script for the desired design. The dental laboratory then pours a refractory material impression based on the initial impression, resulting in an investment model. A second pouring in of the negative dental impression is made in die stone, which results in a finishing model. Both the refractory model and the die stone model are cleaned and trimmed on a lathe. Both the refractory model and the die stone model are positive, or convex molds that duplicate the shape and contours of the target tooth 14.

A clump of wax is set onto the facial surface of the refractory model in the desired location and the wax is carved with the chosen design. The final ornamental appliance 10 will look exactly like the wax model and will be produced using the lost wax technique of casting metals.

Alternatively, a permanent mold of the desired jewelry design may be used. A permanent mold having the negative impression of the desired design is made. That mold is then filled with wax or plastic to create a positive of the desired design, that is, a positive relief of the desired appliance that will become the negative mold for the final ornamental appliance 10. The wax or plastic will melt from the mold, as described below. Plastic models are easier to store than wax impressions and permit greater detail. When a positive relief model is made from a permanent mold, it is attached to the refractory model 16 of the target tooth 14 with a thin layer of wax, which insures that the final ornamental appliance 10 will have a rear surface that conforms exactly to the contours of the target tooth 14 in the exact area to which the ornamental appliance 10 will be attached.

Figure 13:
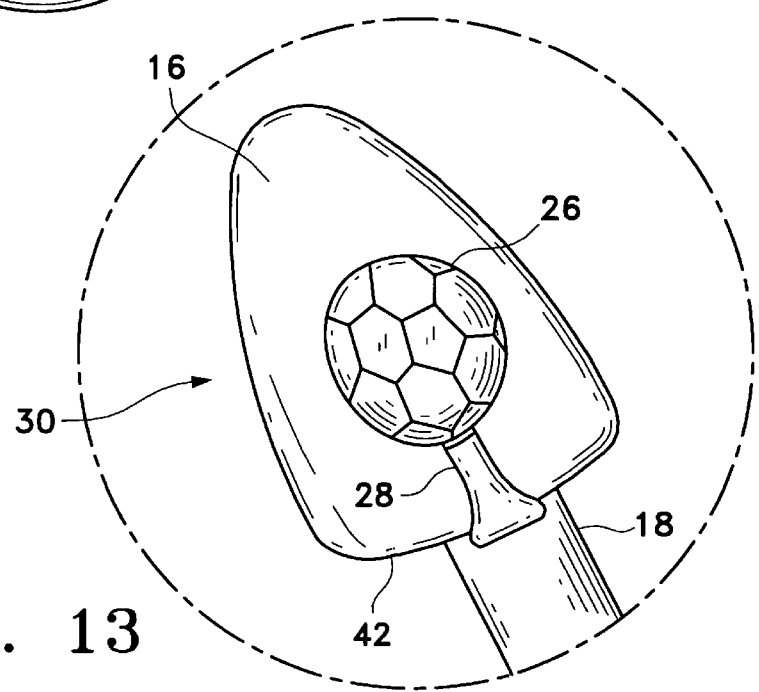
FIG. 13 is an enlarged detail of the circled portion of FIG. 8.

Referring to FIGS. 8–10, the refractory model 16 of the target tooth 14, with the previously carved wax model 26 of the ornamental appliance 10 is sprued, that is, a wax rod, or sprue 28 is permanently attached to the wax model 26 lead. The wax rod 28 runs from the edge of the wax model 26 closest to the incisal edge of the refractory mold 16 of the target tooth 14 to and over the incisal edge. Then the mold assembly 30, consisting of the refractory model 16, attached wax model 26 and sprue 28, is attached to a large wax rod, or branch sprue 18 of the model tree 20 supported by the tree base 22, which is set into a sprue base 24. This allows multiple designs to be invested in one ring or flask 38 (FIGS. 9, 10). When the metal is cast for the final design, the molten metal will flow along the direction of the sprues 28 and branch sprues 18. When the wax portions are lost, the sprues 18, 28 become conduits for the molten metal on its way to the mold. FIG. 13 shows an enlarged view of the left-hand side mold assembly 30, providing more detail.

Then the sprued tree 32 is set into the sprue base 22, typically a rubber disk, whose inner rim 34 contains a wad of pliable wax 36 into which the sprue tree is inserted. The flask 38, which is a stainless steel cylinder open at both ends, is set into the rubber sprue base 24, creating a leak-proof vessel to pour the investment material into.

The investment 40 is a type of plaster that does not burn or crack under very high temperatures. The investment 40 is mixed with water to form a slurry, which is poured into the flask 38, completely submerging the contents of the flask 38. After the investment slurry sets into a solid block of investment 40, the sprue base 24 is removed from the flask 38. As shown in FIG. 10, the flask 38 and contents are ready for heating. In reality, the refractory model 16 of the target tooth 14 becomes bound up with and substantially indistinguishable from the investment 40 when the investment 40 hardens, but the refractory models 16 are shown in FIG. 10 for conceptual clarity.

The flask 38 and contents, including the hardened investment 40 encapsulating the mold assemblies 30, pliable wax wad 36, tree base 22, branch sprue 18, refractory model 16, sprues 28 and branch spruces 18, is placed in a burn out oven with the sprues 18, 28 running down. The temperature of the oven is gradually increased and the wax from the sprues 18, 28 and the wax from the wax model 26 melts and flows out of the bottom of the flask 38. Any residue of wax inside the flask 38 vaporizes and escapes through the pours in the investment. Final temperatures achieved for this step range from 1,000–1,400 degrees F. When all wax is completely burned out of the flask 38, the resulting cavities form a negative mold to receive the molten metal used to cast the final designs.

A casting machine (not shown) shoots molten metal, gold or other metals, into the mold voids or cavities in the investment 40, which were occupied by wax prior to heating in the oven. The molten metal is forced into the cavities by force, typically in a centrifuge, forcing the molten metal into the opening at the bottom of the flask 38 and through the network of sprues and molds described above, filling all the voids formed when the wax or other material melted. The flask 38 and its contents are cooled by cold running water and then the investment 40 is broken away from the metal pieces using a hammer. During investing and heating, the refractory model 16 of the target tooth becomes incorporated into the investment 40 and is therefore lost when the investment 40 is broken away from the metal pieces.

Figure 11:
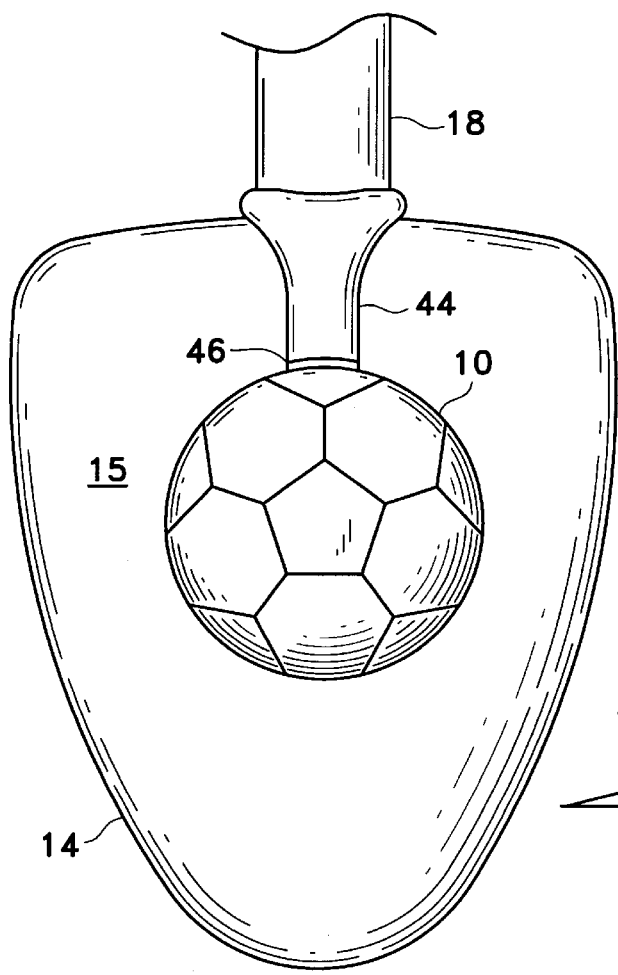
FIG. 11 is an inverted front elevation of a tooth with an ornamental appliance and its indexing tab shown as the appliance is being installed.
Figure 12:
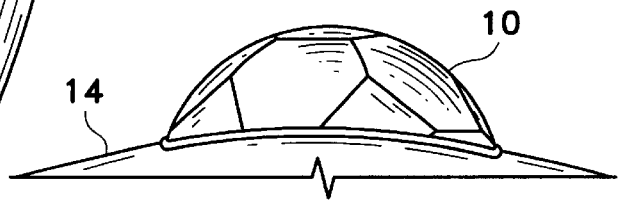
FIG. 12 is a bottom plan view of the tooth and appliance of FIG. 10 after installation is completed.

The final cast pieces, that is, the ornamental appliances 10, are dull and may have surface imperfections. They are cut from the branch sprues 18 by a high speed burr, leaving the sprue 28 extending from the ornamental appliance 10 to the point where the incisal edge 42 of the refractory mold 16 of the target tooth 14 was prior to casting with metal. This leaves an indexing tab 44 (FIG. 11) attached to the ornamental appliance 10, that allows for perfect registration of the ornamental appliance 10 on the target tooth 14. All bubbles or other imperfections are removed by abrasive action such as drilling and grinding and the ornamental appliance 10 is seated on the die stone model of the tooth and the rear surface of the ornamental appliance 10 is treated by abrasive action to remove any imperfections and to assure a good fit with the target tooth 14. The laboratory workers then score the indexing tab 44 adjacent to the ornamental appliance 10, using a high speed burr to create the score line 46, which allows the dentist to break off the indexing tab 44 easily after installation of the ornamental appliance 10. Then the ornamental appliance 10 is polished until it gleams. Then the rear surface 12 of the ornamental appliance is etched with hydrochloric and nitric acids to create a network of microscopic fissures, visible only with the use of an electron microscope, to provide additional surface areas for bonding to the target tooth. The ornamental appliance 10 is shipped to the dentist for installation on the target tooth.

The rear surface 12 of the ornamental appliance resulting from the process described above is an exact negative impression of the corresponding facial surface 15 of the target tooth 14. The indexing tab 44 includes a lip 45 that lies along the incisal edge 42 of the target tooth 42, and the dentist can slide the indexing tab back and forth over the incisal edge 42 until it slides into the exact position required for perfect registration of the ornamental appliance 10 with the desired area of the target tooth 14.

The dentist can feel the point of perfect alignment easily because it is the place at which the ornamental appliance 10 and attached indexing tab 44 experiences the greatest resistance to applied force trying to move the appliance 10 and indexing tab 44 to another position. The registration of the ornamental appliance 10 with the facial surface 15 of the target area of the target tooth 14 provides better adhesion with a thinner layer of cement being required and thereby resulting in better stability and retention.

As shown in FIG. 3, the ornamental appliance 10 is attached to the target tooth 14, which in the case illustrated is the left central incisor, by cementing the ornamental appliance 10 to the labial surface of the target tooth 14. The labial surface of any particular target tooth can be entirely covered by an ornamental appliance 10, or any portion of it. Alternatively, the ornamental appliance may cover all or part of the labial surface of a target tooth and include a shaped cut-out portion that reveals a design in the white enamel of the tooth, or may cover the entire labial surface of a target tooth and include a raised base-relief design or pattern.

Figure 5:
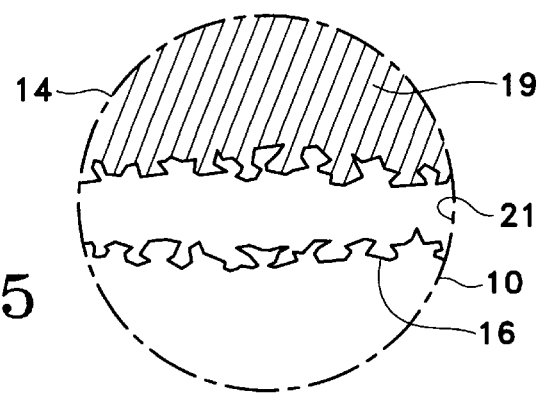
FIG. 5 is an enlarged fragmentary view of the area encompassed by the circle 5 of FIG. 4.

Prior to fixing the ornamental appliance 10 to the surface of the tooth 14, the tooth 14 is etched with phosphoric acid, which creates a labyrinth of tiny pits and fissures, again, visible only with an electron microscope. This step creates a greater surface area for bonding the ornamental appliance 10 without discoloring the tooth. FIG. 5 illustrates the resulting ornamental appliance 10 fissures 16 and the resulting fissures 19 in the target tooth 14, with the very thin boundary between them being filled by a bonding material 21. Installation is accomplished by coating the rear surface 12 the ornamental appliance 10 with a suitable compatible cement and applying an appropriate catalyst to the surface of the target tooth 14 in the desired area. After the prescribed time of approximately 30 seconds passes, the ornamental appliance 10 is pressed into position firmly by the dentist, using his hand. Moderate hand force is applied for a few seconds, ranging from about 3–15 seconds, and then the patient is instructed not to move his mouth for about two minutes, allowing the cement to cure entirely.

The dentist bends the indexing tab 44 along a score line 46 adjacent to the ornamental appliance 10 and removes the indexing tab 44, which can be returned to the laboratory for recycling. The process is now complete and the ornamental appliance 10 is permanently installed on the target tooth 14.

The ornamental appliance 10 can be removed by a dentist if the patient so desires and can either be replaced with a new or different design ornamental appliance 10, or the tooth can be left in its normal condition.

Other embodiments and techniques for carrying out the present invention may be conceived. For example, the ornamental appliances may be cast in plastic resins or mixed two part or light-triggered monomers.

While the present invention has been described in accordance with the preferred embodiments thereof, the description is for illustration only and should not be construed as limiting the scope of the invention. Various changes and modifications may be made by those skilled in the art without departing from the spirit and scope of the invention as defined by the following claims.

We claim:

1. An ornamental appliance for attaching to a surface of a tooth comprising a precious metal design further comprising a tooth-facing surface molded to register with a specific location on the facial surface of a target tooth to which said ornamental dental appliance will be attached and further comprising an indexing tab connected to an outer edge of said ornamental dental appliance, said indexing tab further comprising a lip having an inner lengthwise edge molded to the shape of an incisal cutting edge of said target tooth to provide an indexing tab that provides exact registration of said ornamental appliance along said incisal cutting edge of said target tooth and between said incisal cutting edge and a root of said tooth on said target tooth.

2. An ornamental dental appliance in accordance with claim 1 further comprises an etched tooth-facing surface.

3. An ornamental dental appliance in accordance with claim 1 further comprising a score line across said indexing tab adjacent to said ornamental dental appliance.

* * * * *